United States Patent [19]

Salbeck et al.

[11] 4,278,461
[45] Jul. 14, 1981

[54] HERBICIDAL AGENTS

[75] Inventors: Gerhard Salbeck, Hofheim; Hubert Schönowsky, Urberach; Gerhard Hörlein, Frankfurt am Main; Peter Langelüddeke, Diedenbergen; Helmut Köcher, Hofheim, all of Fed. Rep. of Germany

[73] Assignee: Hoechst Aktiengesellschaft, Frankfurt am Main, Fed. Rep. of Germany

[21] Appl. No.: 942,069

[22] Filed: Sep. 13, 1978

Related U.S. Application Data

[63] Continuation of Ser. No. 764,963, Feb. 2, 1977, abandoned.

[30] Foreign Application Priority Data

Feb. 4, 1976 [DE] Fed. Rep. of Germany ....... 2604224

[51] Int. Cl.$^3$ .......................... A01N 57/14; C07F 9/40
[52] U.S. Cl. .......................................... 71/87; 260/943
[58] Field of Search ........................... 71/87; 424/211; 260/943

[56] References Cited

U.S. PATENT DOCUMENTS

| | | | |
|---|---|---|---|
| 3,032,466 | 5/1962 | Schuler | 424/211 |
| 3,057,774 | 10/1962 | Baker et al. | 424/211 |
| 3,102,019 | 8/1963 | Speziale et al. | 71/87 |
| 3,385,689 | 5/1968 | Richter | 71/87 |
| 4,023,956 | 5/1977 | Yoshida et al. | 71/87 |

FOREIGN PATENT DOCUMENTS 1122935 2/1962 Fed. Rep. of Germany .
2320371 7/1974 Fed. Rep. of Germany .

*Primary Examiner*—Catherine L. Mills
*Attorney, Agent, or Firm*—Curtis, Morris & Safford

[57] ABSTRACT

Herbicidal agents containing as active ingredient a compound of the formula

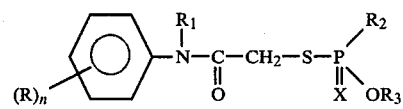

in which R represents halogen, $C_1$–$C_4$-alkyl, $C_1$–$C_2$-alkoxy or $C_1$–$C_2$-alkylthio, $C_1$–$C_2$-halogeno-alkyl, $NO_2$-$SO_2CH_3$, $SO_2NH_2$, —$COOCH_3$, CN, with the proviso that $R_2$ cannot be alkoxy when $(R)_n$ is alkyl, $R_1$ and $R_3$ represent $C_1$–$C_6$-alkyl, $R_2$ represents $C_1$–$C_6$-alkyl, $CH_2Cl$ or $C_1$–$C_6$-alkoxy, X is oxygen or sulfur and n is an integer of from 1 to 3 are especially useful for combatting annual weed grasses in dicotyledonous and even monocotyledonous crop plants.

11 Claims, No Drawings

HERBICIDAL AGENTS

This is a continuation, of application Ser. No. 764,963 filed Feb. 2, 1977 now abandoned.

The subject of the invention is herbicidal agents that contain as active substance a compound of the general formula I

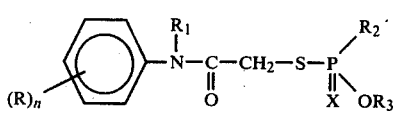

in which

R represents the same or different radicals from the group halogen ($C_1$-$C_4$)-alkyl, ($C_1$-$C_2$)-alkoxy or ($C_1$-$C_2$)-alkylthio, ($C_1$-$C_2$)-halogenoalkyl, $NO_2$, $SO_2CH_3$, $SO_2NH_2$, —$COOCH_3$, CN, with the proviso that $R_2$ cannot be alkoxy when $(R)_n$ is alkyl, $R_1$ and $R_3$ represent ($C_1$-$C_6$)-alkyl, $R_2$ represents ($C_1$-$C_6$)-alkyl, $CH_2Cl$, or ($C_1$-$C_6$)-alkoxy, X represents oxygen or sulfur and n is an integer of from 1–3.

The compounds of the formula I have already partly been described in U.S. Pat. No. 3,057,774 and DT-AS No. 1 122 935, an insecticides and/or miticidal agents. Herbicidal properties were not described therein. On the other hand, it is known that (di)-thiophosphoric acid-N-arylcarbamoyl esters, which may optionally be substituted in the aryl radical by alkyl radicals, and chloromethane-(di)-thiophosphoric acid-N-phenylcarbamoyl esters exhibit herbicidal activity (U.S. Pat. No. 3,102,019 and DT-OS No. 2 320 371).

Preferred radicals of the general formula I are:

R=F, Cl, Br, ($C_1$-$C_4$)-alkyl, $CF_3$, $NO_2$, $SCH_3$ with the proviso that $R_2$ cannot be alkoxy when $(R)_n$ is alkyl, $R_1$ and $R_3$ = ($C_1$-$C_4$)-alkyl, $R_2$ = ($C_1$-$C_4$)-alkyl, $CH_2Cl$ or ($C_1$-$C_4$)-alkoxy.

Particularly preferred are compounds in which R=F, Cl and/or Br. As herbicides they are suitable in particular for combatting annual weed grasses in important dicotyledonous plants and in some cases also in monocotyledonous crop plants.

It is possible with the agents according to the invention to combat, for example, annual backgrass in sugar beet or rape in the same way as crabgrass, foxtail or barnyard grass in leguminous or vegetable plants; it is however, also possible to eradicate grass-type weeds in grass-type plants, such as barnyard grass in rice or blackgrass in oats.

Other types of crop, such as, for example, celery, tomato, spinach, sunflower, cucumber and flax likewise permit good control of grass-type weeds without becoming damaged by the use of the agents according to the invention.

As a result of this action against grass-type weeds, chiefly couch grass, hen grass and bristle grass inter alia, the new agents of the formula I are superior to conventional agents, for example Alachlor and Butachlor, when applied to fields that are strongly infested with grass-type weeds. The quantities required for the complete eradication of the grass-type weeds are, moreover, not as great as in the case of the above-mentioned known herbicides.

Also advantageous is the fact that the compound of the formula I is substantially non-toxic to warm blooded animals in comparison with the compounds of U.S. Pat. No. 3,102,019, as is apparent from the following comparison:

Compound according to U.S. Pat. No. 3,102,019

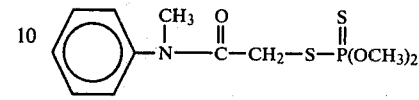

LD$_{50}$ oral
white mouse
mg/kg
11.6

Compound according to the application

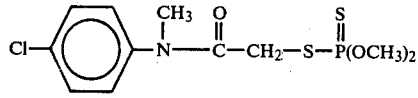

210.0

The compounds of the formula I are produced according to methods known per se, such as are described, for example, in the Patents already mentioned, for example by reacting compounds of the formula II

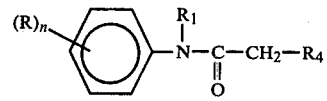

optionally in the presence of an acid-binding agent, with phosphorus compounds of the formula III

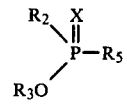

in which in each case one of the radicals $R_4$ and $R_5$ represents a halogen, in particular chlorine or bromine, and the other represents the SY-group, in which Y is hydrogen or a metal cation.

The thioglycolic acid anilides according to formula II may be produced by methods known in the literature. The halogeno-phosphorus compounds of the formula III are known and are readily obtainable by usual methods.

The agents according to the invention contain the active substances of the formula I generally in a proportion of 2–95% by weight. They can be used in the form of wettable powders, emulsifiable concentrates, sprayable solutions, dusting agents or granulates in the usual preparations.

Wettable powders are preparations that can be dispersed uniformly in water, which in addition to the active substances and apart from a diluent or inert substance also contain wetting agent, for example, polyoxethylated alkyl phenols, polyoxethylated oleyl or stearyl amines, alkyl sulfonates or alkylphenyl sulfonates and a dispersing agent, for example, a sodium salt of ligninsulphonic acid, sodium salt of 2,2'-dinaphthylmethan-6,6'-disulphonic acid a sodium salt of dibutylnaphthalene-sulphonic acid or also a sodium salt of oleylmethyltaurine acid.

Emulsifiable concentrates are obtained by dissolving the active substance in an organic solvent, for example butanol, cyclohexanone, dimethyl formamide, zylene or also aromatic substances having relatively high boiling points.

To obtain good suspensions or emulsions in water, in addition wetting agents from the above-mentioned series are added.

Dusting agents are obtained by grinding the active substance with finely divided, solid substances, for example talcum, natural clays, such as kaolin, bentonite, pyrophyllite or diatomaceous earths.

Sprayable solutions, as often sold in spray cans, contain the active substance dissolved in an organic solvent, and in addition there is also to be found therein, for example as propellant, a mixture of fluorochlorohydrocarbons.

Granulates can be produced either by spraying the active substance onto adsorptive, granulated inert material, or by applying active substance concentrates by means of adhesives, for example, polyvinyl alcohol, a sodium salt of polyacrylic acid, or also mineral oils, to the surface of carrier substances, such as sand and kaolinites, or to the surface of granulated inert material. Also, suitable active substances can be produced in the manner customary for the production of granulated manure—optionally in admixture with manure.

The concentrations of the active substances in the herbicidal agents may vary in the commercially customary formulations. In wettable powders, the active substance concentration varies, for example, between approximately 10% and 95%; the remainder consists of the above-mentioned additives. In emulsifiable concentrates, the active substance concentration is approximately 10% to 80%. Dust-type preparations contain usually 5-20% of active substance, sprayable solutions approximately 2-20%. In the case of granulates, the content of active substance depends to some extent on whether the active compound is liquid or solid and on which granulating auxiliaries, fillers etc. are used.

For application, the concentrates that are commercially customary are optionally diluted in the usual manner, for example in the case of wettable powders and emulsifiable concentrates by means of water. Dust-type and granulated preparations as well as sprayable solutions are not diluted with further inert substances before application. The required quantity to be applied varies in accordance with the external conditions, such as temperature, humidity etc. It is generally approximately 0.1-10 kg/ha, preferably approximately 0.15 to 2.5 kg/ha of active substance. The active substance according to the invention can be combined with other herbicides and soil insecticides.

There come into consideration as herbicides that are suitable for combination with the claimed new product, for example, the following compounds listed by their common names or chemical names:

| | |
|---|---|
| Urea derivatives | Linuron, Monolinuron, Chlortoluron, Isoproturon, Metoxuron, Fluometuron, Diuron, Methabenzthiazuron; |
| Triazine derivatives | Simazine, Atrazine, Ametryne, Prometryne, Desmetryne, Methoprotryne, Metribuzin; |
| Uracil derivatives | Lenacil, Bromacil; |
| Phenoxy-alkanecarboxylic acids | 2,4-D, MCPA, Dichlorprop, Mecoprop, 2,4-DB, TBA; |
| Carbamic acid derivatives | Barban, Phenmedipham, Di-allate, Tri-ellate, Vernolate, Benthiocarb, Swep; |
| Dinitrophenol derivatives | DNOC, DNBP (Dinoseb), Dinoterb and the esters and salts thereof |
| Chlorinated aliphatic acids | TCA, Dalapon; |
| Amides | Diphenamide, Isocarboxide; |
| Anilides | Propanil, Solan, Monalide, Alachlor, Propachlor, Butachlor; |
| Anilines | Trifluralin, Nitralin, Oryzalin, Dinitramin; |
| Dipyridillium Compounds | Paraquat, Diquat; |
| Other active substance groups | Dichlobenil, Ioxynil, Cyanazine, Pyrazone, Bromofenoxim, Chlorthalmethyl, Benzoylpropethyl, Chlorphenpropmethyl, MSMA, DSMA, Nitrofen, Flurenol, Bentazol, Fluorodifen. |

Another form of application of the active substance in question consists in its mixture with manure, whereby agents that simultaneously have fertilizing and herbicidal action are obtained.

FORMULATION EXAMPLES

Example A

A wettable powder that is readily dispersible in water is obtained by mixing 25 parts by weight of dithiophosphoric acid-S-[N-(4-chlorophenyl)-N-isopropyl-carbamoylmethyl]-O,O-diethyl ester as active substance, 64 parts by weight of kaolin-containing quartz as inert substance, 10 parts by weight of a potassium salt of ligninsulphonic acid and 1 part by weight of a sodium salt of oleylmethyltaurine acid as wetting and dispersing agent
and grinding in a pinned disk mill.

EXAMPLE B

A dusting agent, that is well suited to application as a weed-destroying agent, is obtained by mixing and comminuting in a hammer mill 10 parts by weight of dithiophosphoric acid-S[N-(4-chlorophenyl)-N-isopropyl-carbamoylmethyl]-O,O-diethyl ester as active substance and 90 parts by weight of talcum as inert substance.

Example C

An emulsifiable concentrate consists of 15 parts by weight of dithiophosphoric acid-S[N-(4-chlorophenyl)-N-isopropyl-carbamoylmethyl]-O,O-diethyl ester, 75 parts by weight of cyclohexanone as solvent and 10 parts by weight of oxethylated nonylphenol (10 AeO) as emulsifer.

Example D

A granulate consists, for example, of approximately 2-15 parts by weight of dithiophosphoric acid-S[N-(4-chlorophenyl)-N-isopropyl-carbamoylmethyl]-O,O-diethyl ester
and inert granulate carrier materials, such as, for example, attapulgite, pumice granulate and quartz sand.

MANUFACTURING EXAMPLES

General directions 0.1 mole of a chloroacetanilide of the formula II ($R_4$=Cl) are added at room temperature, while stirring, to a solution or suspension of 0.10–0.11 mole of an ammonium salt of a phosphorus compound of the formula III ($R_5$=SNH$_4$) in 200 ml of glycol dimethyl ether. Stirring is carried out for approximately 3–5 hours at 50° C., the precipitated salt is suction filtered, the filtrate is diluted with approximately 400 ml of benzene, the organic phase is thoroughly washed with water and dried over sodium sulfate.

After distilling off the solvent, the products of the process remain in the form of oils which partially crystallise on grinding.

The compounds of the formula I compiled in the following table were obtained according to the above-mentioned process, and their composition was confirmed by elemental analysis. They are characterised by refractive index and/or melting point.

TABLE 1

$$\underset{(R)_n}{\text{Ar}}\!-\!\underset{R_1}{\text{N}}\!-\!\underset{\underset{O}{\|}}{\text{C}}\!-\!CH_2\!-\!S\!-\!\underset{\underset{X}{\|}}{P}\underset{OR_3}{\overset{R_2}{\diagup}}$$

| Example | $R_{(n)}$ | $R_1$ | $R_2$ | $R_3$ | X | $n_D$ or Mp. |
|---|---|---|---|---|---|---|
| 1 | 2-F | —CH(CH$_3$)$_2$ | —OCH$_3$ | —CH$_3$ | S | $n_D^{23}$: 1.5372 |
| 2 | 2-F | —CH(CH$_3$)$_2$ | —OC$_2$H$_5$ | —C$_2$H$_5$ | S | Mp. 41–45° C. |
| 3 | 2-F | —CH(CH$_3$)$_2$ | —OC$_3$H$_7$(n) | —C$_3$H$_7$(n) | S | $n_D^{24}$: 1.5286 |
| 4 | 3-F | —CH(CH$_3$)$_2$ | —OC$_2$H$_5$ | —C$_2$H$_5$ | S | Mp. 50–56° C. |
| 5 | 3-F | —CH(CH$_3$)$_2$ | —OC$_3$H$_7$(n) | —C$_3$H$_7$(n) | S | $n_D^{24}$: 1.5300 |
| 6 | 4-F | —CH(CH$_3$)$_2$ | —OCH$_3$ | —CH$_3$ | S | $n_D^{24}$: 1.5433 |
| 7 | 4-F | —CH(CH$_3$)$_2$ | —OC$_2$H$_5$ | —C$_2$H$_5$ | S | Mp. 33–35° C. |
| 8 | 4-F | —CH(CH$_3$)$_2$ | —OC$_2$H$_5$ | —C$_2$H$_5$ | O | $n_D^{24}$: 1.5072 |
| 9 | 4-F | —CH(CH$_3$)$_2$ | —OCH(CH$_3$)$_2$ | —CH(CH$_3$)$_2$ | S | Mp. 66–29° C. |
| 10 | 4-F | —CH(CH$_3$)$_2$ | —OC$_3$H$_7$(n) | —C$_3$H$_7$(n) | S | $n_D^{21}$: 1.5224 |
| 11 | 4-F | —CH(CH$_3$)$_2$ | —OC$_4$H$_9$(n) | —C$_4$H$_9$(n) | S | $n_D^{24}$: 1.5610 |
| 12 | 2-Cl | —CH$_3$ | —OC$_2$H$_5$ | —C$_2$H$_5$ | S | $n_D^{24}$: 15473 |
| 13 | 2-Cl | —CH$_3$ | —OC$_2$H$_5$ | —C$_2$H$_5$ | O | Mp. 66–69° C. |
| 14 | 3-Cl | —CH$_3$ | —OC$_2$H$_5$ | —C$_2$H$_5$ | S | $n_D^{21}$: 1.5639 |
| 15 | 3-Cl | —CH$_3$ | —OC$_2$H$_5$ | —C$_2$H$_5$ | O | $n_D^{23}$: 1.5323 |
| 16 | 4-Cl | —CH(CH$_3$)$_2$ | —OCH$_3$ | —CH$_3$ | S | $n_D^{24}$: 1.5610 |
| 17 | 4-Cl | —CH(CH$_3$)$_2$ | —OC$_2$H$_5$ | —C$_2$H$_5$ | S | $n_D^{24}$: 1.5530 |
| 18 | 4-Cl | —CH(CH$_3$)$_2$ | —OC$_2$H$_5$ | —C$_2$H$_5$ | O | $n_D^{23}$: 1.5233 |
| 19 | 4-Cl | —CH(CH$_3$)$_2$ | —OC$_3$H$_7$(n) | —C$_3$H$_7$(n) | S | $n_D^{24}$: 1.5416 |
| 20 | 4-Cl | —C$_2$H$_5$ | —OC$_2$H$_5$ | —C$_2$H$_5$ | S | $n_D^{25}$: 1.5579 |
| 21 | 4-Cl | —C$_2$H$_5$ | —OC$_3$H$_7$(n) | —C$_3$H$_7$(n) | S | $n_D^{25}$: 1.5457 |
| 22 | 4-Cl | —C$_2$H$_5$ | —OCH$_3$ | —CH$_3$ | S | $n_D^{25}$: 1.5686 |
| 23 | 4-Cl | —C$_2$H$_5$ | —OC$_2$H$_5$ | —C$_2$H$_5$ | O | $n_D^{23}$: 1.5330 |
| 24 | 4-Cl | —C$_4$H$_9$(sec.) | —OCH$_3$ | —CH$_3$ | S | $n_D^{24}$: 1.5586 |
| 25 | 4-Cl | —C$_4$H$_9$(sec.) | —OC$_2$H$_5$ | —C$_2$H$_5$ | S | $n_D^{24}$: 1.5457 |
| 26 | 4-Cl | —C$_4$H$_9$(sec.) | —OC$_2$H$_5$ | —C$_2$H$_5$ | O | $n_D^{24}$: 1.5198 |
| 27 | 4-Cl | —C$_4$H$_9$(sec.) | —OC$_3$H$_7$(n) | —C$_3$H$_7$(n) | S | $n_D^{24}$: 1.5386 |
| 28 | 4-Cl | —CH$_3$ | —OC$_2$H$_5$ | —C$_2$H$_5$ | S | $n_D^{24}$: 1.5609 |
| 29 | 4-Cl | —CH$_3$ | —OC$_2$H$_5$ | —C$_2$H$_5$ | O | $n_D^{21}$: 1.5323 |
| 30 | 4-Br | —CH(CH$_3$)$_2$ | —OCH$_3$ | —CH$_3$ | S | Mp. 67–70° C. |
| 31 | 4-Br | —CH(CH$_3$)$_2$ | —OC$_2$H$_5$ | —C$_2$H$_5$ | S | Mp. 62–65° C. |
| 32 | 4-Br | —CH(CH$_3$)$_2$ | —23: 2H$_5$ | —C$_2$H$_5$ | O | Mp. 71–74° C. |
| 33 | 4-Br | —3)$_2$ | —OC$_3$H$_7$(n) | —C$_3$H$_7$(n) | S | Mp. 66–70° C. |
| 34 | 2,3-Cl | —CH$_3$ | —OC$_2$H$_5$ | —C$_2$H$_5$ | S | $n_D^{21}$: 1.5767 |
| 35 | 2,3-Cl | —CH$_3$ | —OC$_2$H$_5$ | —C$_2$H$_5$ | O | $n_D^{21}$: 1.5385 |
| 36 | 2,4-Cl | —CH$_3$ | —OC$_2$H$_5$ | —C$_2$H$_5$ | S | $n_D^{27}$: 1.5610 |
| 37 | 2,4-Cl | —CH$_3$ | —OC$_2$H$_5$ | —C$_2$H$_5$ | O | $n_D^{24}$: 1.5382 |
| 38 | 2,5-Cl | —CH$_3$ | —OC$_2$H$_5$ | —C$_2$H$_5$ | S | $n_D^{27}$: 1.5702 |
| 39 | 2,5-Cl | —CH$_3$ | —OC$_2$H$_5$ | —C$_2$H$_5$ | O | $n_D^{27}$: 1.5548 |
| 40 | 3,4-Cl | —CH$_3$ | —OC$_2$H$_5$ | —C$_2$H$_5$ | S | $n_D^{22}$: 1.5700 |
| 41 | 3,4-Cl | —CH$_3$ | —OC$_2$H$_5$ | —C$_2$H$_5$ | O | $n_D^{23}$:177 1.5432 |
| 42 | 3,5-Cl | —CH$_3$ | —OC$_2$H$_5$ | —C$_2$H$_5$ | S | Mp. 62°62–65° C. |
| 43 | 3,5-Cl | —CH$_3$ | —OC$_2$H$_5$ | —C$_2$H$_5$ | O | $n_D^{24}$: 1.5410 |
| 44 | 2,4-F | —CH(CH$_3$)$_2$ | —OCH$_3$ | —CH$_3$ | S | $n_D^{23}$: 1.5320 |
| 45 | 2,4-F | —CH(CH$_3$)$_2$ | —OC$_2$H$_5$ | —C$_2$H$_5$ | S | $n_D^{23}$: 1.5270 |
| 46 | 2,4-F | —CH(CH$_3$)$_2$ | —OC$_3$H$_7$(n) | —C$_3$H$_7$( ) | S | $n_D^{23}$: 1.5212 |
| 47 | 3-Cl, 4-F | —CH(CH$_3$)$_2$ | —OC$_2$H$_5$ | —C$_2$H$_6$ | S | $n_D^{23}$: 1.5425 |
| 48 | 3-Cl, 4-F | —CH(CH$_3$)$_2$ | —OC$_3$H$_7$(n) | —C$_3$H$_7$(n) | S | $n_D^{23}$: 1.5313 |
| 49 | 3-Cl, 2-F | —CH(CH$_3$)$_2$ | —OCH$_3$ | —CH$_3$ | S | $n_D^{24}$: 1.5565 |
| 50 | 3-Cl, 2-F | —CH(CH$_3$)$_2$ | —OC$_2$H$_5$ | —C$_2$H$_5$ | S | $n_D^{23}$: 1.5430 |
| 51 | 3-Cl, 2-F | —CH(CH$_3$)$_2$ | —OC$_3$H$_7$(n) | —C$_3$H$_7$(n) | S | $n_D^{24}$: 1.5378 |
| 52 | 3-Cl, 4,6-F | —CH(CH$_3$)$_2$ | —OC$_2$H$_5$ | —C$_2$H$_5$ | S | $n_D^{23}$: 1.5397 |
| 53 | 3-Cl, 4,6-F | —CH(CH$_3$)$_2$ | —OC$_3$H$_7$(n) | —C$_3$H$_7$(n) | S | $n_D^{23}$: 1.5322 |
| 54 | 2-NO$_2$ | —CH$_3$ | —OC$_2$H$_5$ | —C$_2$H$_5$ | O | $n_D^{22}$: 1.5380 |
| 55 | 3-NO$_2$ | —CH$_3$ | —OC$_2$H$_5$ | —C$_2$H$_5$ | S | $n_D^{25}$: 1.5727 |
| 56 | 3-NO$_2$ | —CH$_3$ | —OC$_2$H$_5$ | —C$_2$H$_5$ | O | $n_D^{23}$: 1.5446 |
| 57 | 4-NO$_2$ | —C$_2$H$_5$ | —OC$_2$H$_5$ | —C$_2$H$_5$ | O | $n_D^{23}$: 1.5443 |
| 58 | 4-NO$_2$ | —C$_4$H$_9$(n) | —OC$_2$H$_5$ | —C$_2$H$_5$ | S | $n_D^{25}$: 1.5680 |
| 59 | 4-NO$_2$ | —C$_4$H$_9$(n) | —OC$_2$H$_5$ | —C$_2$H$_5$ | O | $n_D^{26}$: 1.5428 |
| 60 | 4-NO$_2$ | —CH$_3$ | —OC$_2$H$_5$ | —C$_2$H$_5$ | S | Mp. 48–53° C. |
| 61 | 4-NO$_2$ | —CH$_3$ | —OC$_2$H$_5$ | —C$_2$H$_5$ | O | Mp. 48–52° C. |
| 62 | 4-NO$_2$ | —CH$_3$ | —OCH$_3$ | —CH$_3$ | S | Mp. 55–62° C. |

TABLE 1-continued $$\underset{(R)_n}{\phantom{X}}\text{-C}_6\text{H}_4\text{-N}(R_1)\text{-C}(=O)\text{-CH}_2\text{-S-P}(=X)(R_2)(OR_3)$$

| Example | R(n) | R₁ | R₂ | R₃ | X | $n_D$ or Mp. |
|---|---|---|---|---|---|---|
| 63 | 3-CF₃ | —CH(CH₃)₂ | —OCH₃ | —CH₃ | S | $n_D^{24}$: 1.5197 |
| 64 | 3-CF₃ | —CH(CH₃)₂ | —OC₂H₅ | —C₂H₅ | S | $n_D^{24}$: 1.5126 |
| 65 | 3-CF₃ | —CH(CH₃)₂ | —OC₃H₇(n) | —C₃H₇(n) | S | $n_D^{24}$: 1.5084 |
| 66 | 3-CF₃ | —C₄H₉(sec.) | —OCH₃ | —CH₃ | S | $n_D^{24}$: 1.5171 |
| 67 | 3-CF₃ | —C₄H₉(sec.) | —OC₂H₅ | —C₂H₅ | S | $n_D^{24}$: 1.5112 |
| 68 | 3-CF₃ | —C₄H₉(sec.) | —OC₂H₅ | —C₂H₅ | O | $n_D^{23}$: 1.4865 |
| 69 | 3-CF₃ | —C₄H₉(sec.) | —OC₃H₇(n) | —C₃H₇(n) | S | $n_D^{23}$: 1.5058 |
| 70 | 3,5-CF₃ | CH(CH₃)₂ | —OCH₃ | —CH₃ | S | Mp. 56–60° C. |
| 71 | 3,5-CF₃ | CH(CH₃)₂ | —OC₂H₅ | —C₂H₅ | S | $n_D^{24}$: 1.4856 |
| 72 | 3,5-CF₃ | CH(CH₃)₂ | —OC₂H₅ | —C₂H₅ | O | $n_D^{24}$: 1.4630 |
| 73 | 3,5-CF₃ | CH(CH₃)₂ | —OC₃H₇(n) | —C₃H₇(n) | S | $n_D^{24}$: 1.4831 |
| 74 | 3-CF₃, 4-OC₂H₅ | CH(CH₃)₂ | —OC₂H₅ | —C₂H₅ | S | $n_D^{21}$: 1.5343 |
| 75 | 4-CN | —CH₃ | —OC₂H₅ | —C₂H₅ | O | Mp. 49–51° C. |
| 76 | 4-CN | —CH₃ | —OC₂H₅ | —C₂H₅ | S | Mp. 64–67° C. |
| 77 | 4-SO₂—CH₃ | —CH(CH₃)₂ | —OCH₃ | —CH₃ | S | $n_D^{27}$: 1.5620 |
| 78 | 4-SO₂—CH₃ | —CH(CH₃)₂ | —OC₂H₅ | —C₂H₅ | S | Mp. 75–80° C. |
| 79 | 4-SO₂—NH₂ | —CH(CH₃)₂ | —OCH₃ | —CH₃ | S | Mp. 102–103° C. |
| 80 | 4-SO₂—NH₂ | —CH(CH₃)₂ | —OC₂H₅ | —C₂H₅ | S | Mp. 128–132° C. |
| 81 | 4-SO₂—NH₂ | —CH(CH₃)₂ | —OC₂H₅ | —C₂H₅ | S | Mp. 100–102° C. |
| 82 | 4-COOCH₃ | —CH(CH₃)₂ | —OCH₃ | —CH₃ | S | Mp. 67–70° C. |
| 83 | 4-COOCH₃ | —CH(CH₃)₂ | —OC₂H₅ | —C₂H₅ | O | $n_D^{23}$: 1.5265 |
| 84 | 4-COOCH₃ | —CH(CH₃)₂ | —OC₂H₅ | —C₂H₅ | S | $n_D^{23}$: 1.5444 |
| 85 | 4-OCH₃ | —CH(CH₃)₂ | —OCH₃ | —CH₃ | S | $n_D^{28}$: 1.5551 |
| 86 | 4-OCH₃ | —CH(CH₃)₂ | —OC₂H₅ | —C₂H₅ | S | $n_D^{27}$: 1.5447 |
| 87 | 4-OCH₃ | —CH(CH₃)₂ | —OC₂H₅ | —C₂H₅ | O | $n_D^{27}$: 1.5192 |
| 88 | 4-F | —CH(CH₃)₂ | —CH₃ | —CH₃ | S | $n_D^{23}$: 1.5565 |
| 89 | 4-F | —CH(CH₃)₂ | —CH₃ | —C₂H₅ | S | $n_D^{23}$: 1.5498 |
| 90 | 4-F | —CH(CH₃)₂ | —C₂H₅ | —C₂H₅ | S | $n_D^{24}$: 1.5454 |
| 91 | 4-F | —CH(CH₃)₂ | —CH₃ | —C₄H₉(i) | S | $n_D^{24}$: 1.5393 |
| 92 | 4-F | —CH(CH₃)₂ | —C₄H₉(i) | —C₄H₉(i) | S | $n_D^{23}$: 1.5282 |
| 93 | 4-F | —CH(CH₃)₂ | —CH₃ | —C₄H₉(i) | O | $n_D^{23}$: 1.5132 |
| 94 | 2-Cl | —CH₃ | —CH₃ | —C₂H₅ | S | $n_D^{24}$: 1.5725 |
| 95 | 3-Cl | —CH₃ | —CH₃ | —C₂H₅ | S | Mp. 53–55° C. |
| 96 | 4-Cl | —CH₃ | —CH₃ | —C₂H₅ | S | $n_D^{23}$: 1.5830 |
| 97 | 4-Cl | —C₂H₅ | —CH₃ | —C₂H₅ | S | $n_D^{25}$: 1.5767 |
| 98 | 4-Cl | —C₂H₅ | —CH₃ | —C₄H₉(i) | O | $n_D^{28}$: 1.5313 |
| 99 | 4-Cl | —C₂H₅ | —C₄H₉(i) | —C₂H₅ | S | $n_D^{25}$: 1.5610 |
| 100 | 4-Cl | —CH(CH₃)₂ | —CH₃ | —CH₃ | S | $n_D^{23}$: 1.5715 |
| 101 | 4-Cl | —CH(CH₃)₂ | —CH₃ | —C₄H₉(i) | O | $n_D^{25}$: 1.5255 |
| 102 | 4-Cl | —CH(CH₃)₂ | —CH₃ | —C₂H₅ | S | $n_D^{25}$: 1.5624 |
| 103 | 4-Cl | —CH(CH₃)₂ | —C₄H₉(i) | —C₄H₉(i) | S | $n_D^{26}$: 1.5455 |
| 104 | 4-Cl | —C₂H₅ | —CH₃ | —C₄H₉(i) | S | $n_D^{24}$: 1.5630 |
| 105 | 4-Cl | —C₄H₉(sec) | —CH₃ | —C₂H₅ | S | $n_D^{24}$: 1.5610 |
| 106 | 4-Cl | —C₄H₉(sec) | —CH₃ | —C₄H₉(i) | S | $n_D^{24}$: 1.5530 |
| 107 | 4-Cl | —C₄H₉(sec) | —CH₃ | —C₄H₉(i) | O | $n_D^{24}$: 1.5271 |
| 108 | 4-Cl | —C₄H₉(sec) | —C₄H₉(n) | —C₂H₅ | S | $n_D^{24}$: 1.5533 |
| 109 | 4-Br | —CH(CH₃)₂ | —CH₃ | —C₄H₉(i) | S | $n_D^{24}$: 1.5636 |
| 110 | 4-Br | —CH(CH₃)₂ | —CH₃ | —C₂H₅ | S | $n_D^{23}$: 1.5783 |
| 111 | 4-Br | —CH(CH₃)₂ | —CH₃ | —C₄H₉(i) | O | $n_D^{23}$: 1.5400 |
| 112 | 4-Br | —CH(CH₃)₂ | —C₄H₉(n) | —C₂H₅ | S | $n_D^{24}$: 1.5676 |
| 113 | 2,3-Cl | —CH₃ | —CH₃ | —C₂H₅ | S | $n_D^{21}$: 1.6012 |
| 114 | 2,4-Cl | —CH₃ | —CH₃ | —C₂H₅ | S | $n_D^{24}$: 1.5902 |
| 115 | 2,5-Cl | —CH₃ | —CH₃ | —C₂H₅ | S | $n_D^{27}$: 1.6003 |
| 116 | 3,4-Cl | —CH₃ | —CH₃ | —C₂H₅ | S | Mp. 94° C. |
| 117 | 3,5-Cl | —CH₃ | —CH₃ | —C₂H₅ | S | Mp. 85–86° C. |
| 118 | 3-CF₃ | —CH(CH₃)₂ | —CH₃ | —C₂H₅ | S | $n_D^{22}$: 1.5228 |
| 119 | 3-CF₃ | —CH(CH₃)₂ | —CH₃ | —C₄H₉(i) | O | $n_D^{25}$: 1.4890 |
| 120 | 3-CF₃ | —CH(CH₃)₂ | —CH₃ | —C₄H₉(i) | S | $n_D^{22}$: 1.5145 |
| 121 | 3-CF₃ | C₄H₉(sec) | —CH₃ | —C₂H₅ | S | $n_D^{24}$: 1.5200 |
| 122 | 3-CF₃ | —C₄H₉(sec) | —CH₃ | —C₄H₉(i) | O | $n_D^{25}$: 1.4910 |
| 123 | 3-CF₃ | —C₄H₉(sec) | —CH₃ | —C₄H₉(i) | S | $n_D^{25}$: 1.5135 |
| 124 | 3-CF₃ | —C₄H₉(sec) | —CH₃ | —C₄H₉(n) | S | $n_D^{24}$: 1.5151 |
| 125 | 4-CN | —CH₃ | —CH₃ | —C₂H₅ | S | Mp. 80–83° C. |
| 126 | 2-NO₂ | —CH₃ | —CH₃ | —C₂H₅ | S | $n_D^{23}$: 1.5882 |
| 127 | 3-NO₂ | —CH₃ | —CH₃ | —C₂H₅ | S | $n_D^{25}$: 1.5914 |
| 128 | 4-NO₂ | —C₂H₅ | —CH₃ | —C₂H₅ | S | Mp. 65–68° C. |
| 129 | 4-NO₂ | —CH(CH₃)₂ | —CH₃ | —C₂H₅ | S | $n_D^{25}$: 1.5732 |
| 130 | 4-NO₂ | —C₄H₉(n) | —CH₃ | —C₂H₅ | S | $n_D^{25}$: 1.5853 |
| 131 | 4-SO₂—CH₃ | —CH(CH₃)₂ | —CH₃ | —C₂H₅ | S | $n_D^{27}$: 1.5660 |
| 132 | 4-SO₂—NH₂ | —CH(CH₃)₂ | —CH₃ | —C₄H₉(i) | O | Mp. 98–105° C. |
| 133 | 4-OCH₃ | —CH(CH₃)₂ | —CH₃ | —C₂H₅ | S | $n_D^{27}$: 1.5592 |
| 134 | 4-OCH₃ | —CH(CH₃)₂ | —CH₃ | —C₄H₉(i) | S | $n_D^{27}$: 1.5482 |
| 135 | 4-OCH₃ | —CH(CH₃)₂ | —CH₃ | —C₄H₉(i) | O | $n_D^{24}$: 1.5262 |
| 136 | 4-CH₃ | —CH(CH₃)₂ | —CH₃ | —C₂H₅ | S | $n_D^{27}$: 1.5453 |
| 137 | 4-CH₃ | —CH(CH₃)₂ | —CH₃ | —C₄H₉(i) | S | $n_D^{27}$: 1.5566 |
| 138 | 2-CH(CH₃)₂ | —CH(CH₃)₂ | —CH₃ | —CH₃ | S | $n_D^{25}$: 1.5575 |

TABLE 1-continued $$\underset{(R)_n}{\underset{|}{\text{Ar}}}-\underset{R_1}{\underset{|}{N}}-\underset{\underset{O}{\parallel}}{C}-CH_2-S-\underset{\underset{X}{\parallel}}{P}\underset{OR_3}{\overset{R_2}{\diagup}}$$

| Example | $R_{(n)}$ | $R_1$ | $R_2$ | $R_3$ | X | $n_D$ or Mp. |
|---|---|---|---|---|---|---|
| 139 | 2-CH(CH$_3$)$_2$ | —CH(CH$_3$)$_2$ | —CH$_3$ | —C$_2$H$_5$ | S | Mp. 64–66° C. |
| 140 | 2-CH(CH$_3$)$_2$ | —CH(CH$_3$)$_2$ | —CH$_3$ | —C$_4$H$_9$(i) | O | $n_D^{23}$: 1.5223 |
| 141 | 2-CH(CH$_3$)$_2$ | —CH(CH$_3$)$_2$ | —CH$_3$ | —C$_4$H$_9$(i) | S | $n_D^{23}$: 1.5420 |
| 142 | 4-CH(CH$_3$)$_2$ | —CH(CH$_3$)$_2$ | —CH$_3$ | —C$_2$H$_5$ | S | $n_D^{25}$: 1.5542 |
| 143 | 4-C(CH$_3$)$_3$ | —CH(CH$_3$)$_2$ | —CH$_3$ | —C$_2$H$_5$ | S | Mp. 54–59° C. |
| 144 | 4-C(CH$_3$)$_3$ | —CH(CH$_3$)$_2$ | —CH$_3$ | —C$_4$H$_9$(i) | S | Mp. 54–59° C. |
| 145 | 4-Cl | —CH$_3$ | —CH$_2$Cl | —C$_2$H$_5$ | S | — |
| 146 | 2-NO$_2$ | —CH$_3$ | —OC$_2$H$_5$ | —C$_2$H$_5$ | S | $n_D^{23}$: 1.5680 |
| 147 | 4-NO$_2$ | —C$_2$H$_5$ | —C$_2$H$_5$ | —OC$_2$H$_5$ | S | M$_{65-69°}$ C. |
| 148 | 4-NO$_2$ | —CH(CH$_3$)$_2$ | —C$_2$H$_5$ | —OC$_2$H$_5$ | O | Mp. 62–66° C. |
| 149 | 3-Cl | —CH(CH$_3$)$_2$ | —C$_2$H$_5$ | —OC$_2$H$_5$ | O | $n_D^{23}$: 1.5265 |
| 150 | 3-Cl | —CH(CH$_3$)$_2$ | —C$_2$H$_5$ | —OC$_2$H$_5$ | S | $n_D^{31}$: 1.5531 |
| 151 | 3,4-Cl | —CH(CH$_3$)$_2$ | —C$_2$H$_5$ | —OC$_2$H$_5$ | O | $n_D^{20}$: 1.5370 |
| 152 | 3,4-Cl | —CH(CH$_3$)$_2$ | —C$_2$H$_5$ | —OC$_2$H$_5$ | S | $n_D^{20}$ 1.5615 |
| 153 | 2,5-Cl | —CH(CH$_3$)$_2$ | —C$_2$H$_5$ | —OC$_2$H$_5$ | S | $n_D^{31}$: 1.5580 |
| 154 | 3,4,5-Cl | —CH$_3$ | —CH$_3$ | —OCH$_3$ | S | Mp. 79–81° C. |
| 155 | 3,4,5-Cl | —CH$_3$ | —C$_2$H$_5$ | —OC$_2$H$_5$ | S | Mp. 64–68° C. |
| 156 | 3,4,5-Cl | —CH$_3$ | —C$_2$H$_5$ | —OC$_2$H$_5$ | O | Mp. 70–73° C. |
| 157 | 3,4,5-Cl | —CH$_3$ | —C$_3$H$_7$—n | —OC$_3$H$_7$—n | S | $n_D^{23}$: 1.5718 |
| 158 | 4-SCH$_3$ | —CH(CH$_3$)$_2$ | —C$_2$H$_5$ | —OC$_2$H$_5$ | O | $n_D^{23}$: 1.5518 |
| 159 | 4-SCH$_3$ | —CH(CH$_3$)$_2$ | —C$_2$H$_5$ | —OC$_2$H$_5$ | S | $n_D^{23}$: 1.5750 |
| 160 | 4-Cl | —C$_2$H$_5$ | —C$_2$H$_5$ | —C$_3$H$_7$—n | S | $n_D^{23}$: 1.5717 |
| 161 | 4-Cl | —C$_2$H$_5$ | —C$_2$H$_5$ | —C$_2$H$_5$ | S | $n_D^{23}$: 1.5765 |
| 162 | 4-Cl | —CH(CH$_3$)$_2$ | —C$_2$H$_5$ | —C$_2$H$_5$ | S | $n_D^{23}$: 1.5671 |
| 163 | 4-Cl | —CH(CH$_3$)$_2$ | —C$_3$H$_7$—n | —C$_2$H$_5$ | S | $n_D^{23}$: 1.5631 |
| 164 | 4-NO$_2$ | —CH$_3$ | —CH$_3$ | —C$_2$H$_5$ | S | Mp. 61–66° C. |
| 165 | 4-NO$_2$ | —CH$_3$ | —CH$_3$ | —C$_4$H$_5$ iso | O | $n_D^{24}$: 1.5590 |
| 166 | 2-CH(CH$_3$)$_2$ | —CH(CH$_3$)$_2$ | —C$_2$H$_5$ | —C$_2$H$_5$ | S | $n_D^{23}$: 1.5494 |
| 167 | H | —CH$_3$ | —CH$_3$ | —C$_2$H$_5$ | S | Mp. 59–61° C. |
| 168 | 2-CH$_3$ | —CH(CH$_3$)$_2$ | —CH$_3$ | —C$_2$H$_5$ | S | $n_D^{29}$: 1.5622 |
| 169 | 3-CH$_3$ | —CH(CH$_3$)$_2$ | —CH$_3$ | —C$_2$H$_5$ | S | $n_D^{29}$: 1.5595 |
| 170 | 4-SCH$_3$ | —CH(CH$_3$)$_2$ | —CH$_3$ | —C$_2$H$_5$ | S | $n_D^{23}$: 1.5938 |
| 171 | 3-Cl | —CH(CH$_3$)$_2$ | —CH$_3$ | —C$_2$H$_5$ | S | Mp. 66–68° C. |
| 172 | 2,5-Cl | —CH(CH$_3$)$_2$ | —CH$_3$ | —C$_2$H$_5$ | S | $n_D^{31}$: 1.5765 |
| 173 | 3,4-Cl | —CH(CH$_3$)$_2$ | —CH$_3$ | —C$_2$H$_5$ | S | $n_D^{29}$: 1.5784 |
| 174 | 3,4,5-Cl | —CH$_3$ | —C$_2$H$_5$ | —C$_2$H$_3$ | S | Mp. 77–79° C. |

EXAMPLES OF APPLICATION

In the biological tests on which the Examples described further below are based, the following method was used:

Seeds of weeds and crops were sown in pots and the preparation according to the invention, in the form of a spray powder was sprayed in different doses onto the soil surface. After 4 weeks standing in a greenhouse, the damage to the weeds and to the crops was determined according to Bolle's scheme (Table).

TABLE

Evaluation scheme according to Bolle (Nachrichtenblatt des Deutschen Pflanzenschutzdienstes 16, 1964, 92–94).

| Numerical Value | Percentage damage to Weeds | | | Crops | | |
|---|---|---|---|---|---|---|
| 1 | 100 | | | 0 | | |
| 2 | 97.5 | to | <100 | >0 | to | 2.5 |
| 3 | 95 | to | <97.5 | >2.5 | to | 5 |
| 4 | 90 | to | <95 | >5 | to | 10 |
| 5 | 85 | to | <90 | >10 | to | 15 |
| 6 | 75 | to | <85 | >15 | to | 25 |
| 7 | 65 | to | <75 | >25 | to | 35 |
| 8 | 32.5 | to | <65 | >35 | to | 67.5 |
| 9 | 0 | to | <32.5 | >67.5 | to | 100 |

EXAMPLE I

In a test carried out according to the above-mentioned method, the compounds from Example (8), (18) and (32) proved exceedingly effective against a range of important weed grasses. Even in the case of a very low dosage of 0.15 kg of active substance/ha a good effect was still achieved. The following were used as a comparison:

A = Alachlor = N-methoxy-α-chloracetate-2,6-diethylanilide.

B = O,O-diethyl-S-(N-isopropyl-N-phenyl)-carbamoyl-methyl-dithiophosphonate (cf. U.S. Pat. No. 3,102,019, Compound C).

Both comparative compounds were considerably weaker than the specified substances (Table I).

TABLE I:

| Compound No. | Dose (kg/ha AS) | Weed evaluation figures Types of plant | | | | |
|---|---|---|---|---|---|---|
| | | ALM | SAL | POA | LOM | ECG |
| 8 | 2.5 | 1 | 1 | 1 | 1 | 1 |
| | 0.6 | 1 | 1 | 1 | 1 | 1 |
| | 0.15 | 3 | 3 | 5 | 1 | 4 |
| 18 | 2.5 | 1 | 1 | 1 | 1 | 1 |
| | 0.6 | 1 | 1 | 1 | 1 | 1 |
| | 0.15 | 1 | 3 | 1 | 2 | 1 |
| 32 | 2.5 | 1 | 1 | 1 | 1 | 1 |
| | 0.6 | 1 | 1 | 1 | 1 | 1 |
| | 0.15 | 1 | 1 | 1 | 3 | 3 |
| A (Comparison) | 2.5 | 2 | 1 | 1 | 1 | 1 |
| | 0.6 | 5 | 3 | 1 | 1 | 3 |
| | 0.15 | 7 | 6 | 3 | 5 | 7 |
| B | 2.5 | 1 | 1 | 1 | 1 | 1 |
| | 0.6 | 4 | 3 | 3 | 4 | 3 |

TABLE I:-continued

| Compound No. | Dose (kg/ha AS) | Types of plant | | | | |
|---|---|---|---|---|---|---|
| | | ALM | SAL | POA | LOM | ECG |
| (Comparison) | 0.15 | 8 | 7 | 8 | 8 | 7 |

ALM = *Alopeourus myosuroides*
SAL = *Setaria lutescens*
POA = *Poa annua*
LOM = *Lolium multiflorum*
ECG = *Echinochloa crus-galli*

EXAMPLE II

In a test carried out according to the above-described method the agents according to the invention were examined for their selectivity with crops. The agents proved to be very compatible with numerous crops. In Table II the evaluation figures for each crop are listed, which tolerated the preparations according to the invention from Example (8), (18) and (32) better than the comparative agent Alachlor. In particular attention is drawn to the important crops sugar beet and cotton, in which the application of the comparative agent Alachlor for combatting weeds is not possible. In addition, the above-mentioned, as well as the other new compounds listed in Example I proved to be extremely compatible with numerous other crops such as spinach, sunflower, cucumber, peanut, dwarf bean, soy bean, field bean, flax, tomato and celery.

TABLE II:

| Crop evaluation figures in which the quantity applied is 2.5 kg AS/ha. | | | | |
|---|---|---|---|---|
| Type of plant | 8 | 18 | 32 | Alachlor |
| Sugar beet | 3 | — | 4 | 7 |
| Cotton | 5 | 4 | 3 | 7 |
| Pea | — | 5 | 4 | 8 |
| Carrot | 3 | 1 | 3 | 7 |
| Rape | 1 | 4 | 2 | 5 |
| Tobacco | 3 | 4 | 2 | 5 |
| Cabbage | 3 | 2 | 2 | 5 |

EXAMPLE III

In a greenhouse test, pots sealed at the bottom and standing 15 cm high were filled with earth and sown with echinochloa-crus-galli or rice. A few days later, as the plants began to emerge, 3 week old rice seedlings were transplanted into pots of the same type. After a few days, when the sown rice and the weed echinchloa had formed 1 to 2 leaves, all pots were filled with water so that the water stood 1–2 cm above the soil surface. The suspended spray powder formulations of the active substances were then added to the water. 4 weeks later the following action was ascertained:

Agents according to the invention require 0.08 to 0.62 kg/ha a.i. for adequate control of the weed echinochloa crus-galli prevalent in rice (adequate control: note 4=90% action), double the dosage was satisfactorily tolerated by the rice. The comparative agent C (Butachlor=C,N-(butoxymethyl)-2-chloro-2′,6′-diethyl-acetanilide) was on the other hand effective only in a very high dosage.

TABLE III:

| Compound No. | kg/ha | Rice transplanted | Rice sown | Echinochloa |
|---|---|---|---|---|
| 4 | 1.25 | 3 | 4 | 2 |
| | 0.6 | 2 | 2 | 3 |

TABLE III:-continued

| Compound No. | kg/ha | Rice transplanted | Rice sown | Echinochloa |
|---|---|---|---|---|
| | 0.3 | 1 | 1 | 4 |
| | 0.3 | 3 | 3 | 3 |
| 7 | 0.15 | 2 | 2 | 3 |
| | 0.08 | 1 | 1 | 4 |
| | 0.3 | 7 | 7 | 2 |
| 8 | 0.15 | 6 | 6 | 3 |
| | 0.08 | 2 | 2 | 4 |
| | 0.6 | 1 | 1 | 3 |
| 16 | 0.3 | 1 | 1 | 4 |
| | 0.15 | 1 | 1 | 6 |
| | 1.25 | 3 | 2 | 2 |
| 30 | 0.6 | 2 | 2 | 3 |
| | 0.3 | 1 | 1 | 3 |
| | 0.3 | 6 | 4 | 3 |
| 32 | 0.15 | 2 | 2 | 4 |
| | 0.08 | 1 | 1 | 5 |
| | 1.25 | 3 | 3 | 2 |
| 45 | 0.6 | 2 | 2 | 3 |
| | 0.3 | 1 | 2 | 4 |
| | 0.6 | 2 | 3 | 2 |
| 6 | 0.3 | 1 | 1 | 3 |
| | 0.15 | 1 | 1 | 4 |
| | 1.25 | 1 | 1 | 2 |
| 10 | 0.6 | 1 | 1 | 3 |
| | 0.3 | 1 | 1 | 4 |
| | 0.62 | 2 | 3 | 3 |
| 17 | 0.31 | 2 | 2 | 3 |
| | 0.15 | 1 | 1 | 4 |
| | 0.15 | 4 | 3 | 3 |
| 18 | 0.08 | 3 | 1 | 3 |
| | 0.04 | 1 | 1 | 6 |
| | 1.25 | 2 | 2 | 3 |
| 31 | 0.62 | 1 | 1 | 4 |
| | 0.31 | 1 | 1 | 6 |
| | 1.25 | 4 | 3 | 3 |
| 47 | 0.62 | 2 | 2 | 3 |
| | 0.31 | 1 | 2 | 4 |
| C | 2.5 | 3 | 2 | 3 |
| (Comparison) | 1.25 | 2 | 2 | 5 |
| | 0.62 | 1 | 1 | 8 |

EXAMPLE IV

In a test carried out according to the above-described method, the compounds of Example (88) and (89) proved to be very effective against some important weed grasses. On average they eradicated the weed grasses better than the comparative agent A.

TABLE IV:

| Compound No. | Dosage (kg/ha AS) | Types of plant | | |
|---|---|---|---|---|
| | | ALM | DIS | SAL |
| 88 | 2.5 | 3 | 1 | 1 |
| | 0.6 | 5 | 5 | 2 |
| | 0.15 | 7 | 8 | 6 |
| 89 | 2.5 | 1 | 1 | 1 |
| | 0.6 | 4 | 2 | 2 |
| | 0.15 | 8 | 7 | 6 |
| A | 2.5 | 5 | 3 | 1 |
| | 0.6 | 8 | 3 | 4 |
| (Comparison) | 0.15 | 9 | 8 | 8 |

ALM = *Alopecurus myosuroides*
DIS = *Digitaria sanguinalis*
SAL = *Setaria lutescens*

EXAMPLE V

In a test carried out according to the above-described method, the compound of Example (90) proved to be extremely effective against a range of important weed grasses. The compound of Example (90) was clearly superior to the comparative herbicide A regarding action against grass-type weeds (Table V).

TABLE V:

| Compound No. | Dosage (kg/ha AS) | Weed evaluation figures | | | |
|---|---|---|---|---|---|
| | | ALM | SAL | ECG | DIS |
| 90 | 2.5 | 1 | 1 | 1 | 1 |
| | 0.6 | 1 | 1 | 2 | 1 |
| | 0.15 | 8 | 1 | 5 | 1 |
| A (Comparison) | 2.5 | 2 | 2 | 1 | 2 |
| | 0.6 | 6 | 3 | 4 | 7 |
| | 0.15 | 8 | 8 | 8 | 9 |

ALM = *Alopecurus myosuroides*,
SAL = *Setaria Lutescens*,
ECG = *Echinochloa crus-galli*,
DIS = *Digitaria sanguinalis*

EXAMPLE VI

In a test for selectivity carried out according to the above-described method, the compounds of Example (88) and (89) as well as (90) were well tolerated by a large range of crops. The mentioned active substances were clearly compatible with sugar beet, lettuce, cotton, peas, field beans, cabbage, cucumber, tomato, tobacco, carots and lucerne in the high dosage of 2.5 kg/ha (Evaluations as far as note 4), whereas the comparative agent A was not compatible; in addition the compounds of Example (88) with oats as well as (89) and (90) with spinach are well tolerated in contrast to A.

The same dosage of the active substances according to the invention were furthermore tolerated by sunflower, rape, peanut, soy bean, dwarf bean, celery and flax.

TABLE VI:

Crop evaluation figures for an application quantity of 2.5 kg of active substance/ha.

| Type of plant | 88 | 89 | 90 | Alachlor |
|---|---|---|---|---|
| Oats | 3 | — | — | 7 |
| Sugar beet | 3 | 2 | 2 | 6 |
| Lettuce | 1 | 2 | 3 | 8 |
| Cotton | 1 | 2 | 1 | 5 |
| Pea | 3 | 1 | 3 | 6 |
| Broad bean | 2 | 4 | 3 | 8 |
| Cabbage | 3 | 3 | 2 | 7 |
| Cucumber | 3 | 3 | 2 | 9 |
| Tomato | 2 | 2 | 3 | 7 |
| Tobacco | 3 | 3 | 1 | 8 |
| Carrot | 2 | 4 | 1 | 9 |
| Spinach | — | 4 | 4 | 8 |
| Lucerne | 3 | 3 | 4 | 8 |

EXAMPLE VII

Rice (as the crop) and echinochloa (as the weed) were sown in pots having a closed base. A few days later, when the plants began to emerge all pots were filled with water so that the water stood approximately 1 cm above the surface of the soil; active substances according to the invention were then applied to the water. 4 weeks after the treatment it was found that the substances had an excellent action against the grass-type weed echinochloa, whereas the rice tolerated the treatment very well.

TABLE VII:

Result of a selective test in rice (evaluation figures)

| Compound No. | Dosage (kg/ha AS) | Rice | Echinochloa |
|---|---|---|---|
| 88 | 1.25 | 1 | 2 |
| | 0.62 | 1 | 3 |
| | 0.31 | 1 | 5 |
| 89 | 1.25 | 3 | 2 |
| | 0.62 | 2 | 3 |
| | 0.31 | 1 | 4 |

EXAMPLE VIII

In a test carried out analogously to that in Example I and II, the active substances of Example (88) and (90) proved to be equally as good, if not better, in the action against weeds than the comparative substance D[O-ethyl-S-(N-methyl-N-phenyl)-carbamoylmethyl-(chloromethyl-dithiophosphonate) cf. DOS No. 2 320 371], but in their selectivity or preservation of the listed crops (Table VIII) proved to be clearly superior to the comparative substance D.

TABLE VIII:

| | Pre-emergence- Action and selectivity (Evaluation figures) | | | | | | | | |
|---|---|---|---|---|---|---|---|---|---|
| | 90 | | | 88 | | | D | | |
| Compound No. | 2.5 | 0.62 | 0.15 | 2.5 | 0.62 | 0.15 | 2.5 | 0.62 | 0.15 |
| Weeds: | | | | | | | | | |
| *Digitaria sanguinalis* | 1 | 1 | 1 | 1 | 2 | 8 | 1 | 1 | 8 |
| *Echinochloa crus-galli* | 1 | 1 | 6 | 1 | 4 | 8 | 1 | 2 | 8 |
| *Setaria lutescens* | 1 | 1 | 1 | 1 | 2 | 6 | 1 | 4 | 8 |
| Crops | | | | | | | | | |
| Transplanted lettuce | 3 | 1 | 1 | 1 | 1 | 1 | 8 | 3 | 1 |
| Transplanted white cabbage | 3 | 1 | 1 | 3 | 1 | 1 | 6 | 3 | 2 |
| Cucumber | 2 | 1 | 1 | 3 | 2 | 1 | 8 | 4 | 3 |
| Soy bean | 1 | 1 | 1 | 1 | 1 | 1 | 5 | 3 | 1 |
| Lucerne | 4 | 2 | 1 | 3 | 2 | 1 | 7 | 2 | 1 |
| Cotton | 1 | 1 | 1 | 1 | 1 | 1 | 6 | 3 | 1 |

EXAMPLE IX

A larger number of compounds according to the invention were examined for action against grass-type weeds by the method described in Example I. Table IX indicates the action of these substances on echinochloa crus-galli (ECG); the action on other grass-type weeds was similar.

TABLE IX

| Compound No. | Action on ECG | | |
|---|---|---|---|
| | 2.5 | 0.6 | 0.15 kg/ha |
| 4 | 1 | 3 | 7 |
| 6 | 1 | 1 | 3 |
| 7 | 1 | 1 | 1 |
| 16 | 1 | 1 | 2 |
| 17 | 1 | 2 | 3 |

TABLE IX-continued

| Compound No. | Action on ECG | | |
|---|---|---|---|
| | 2.5 | 0.6 | 0.15 kg/ha |
| 20 | 1 | 1 | 5 |
| 22 | 1 | 2 | 6 |
| 23 | 1 | 1 | 2 |
| 24 | 1 | 3 | 6 |
| 26 | 1 | 2 | 4 |
| 30 | 1 | 1 | 3 |
| 31 | 1 | 2 | 5 |
| 44 | 1 | 3 | 4 |
| 45 | 1 | 2 | 6 |
| 47 | 1 | 2 | 6 |
| 53 | 4 | 9 | 9 |
| 54 | 2 | 8 | 9 |
| 55 | 1 | 2 | 8 |
| 56 | 1 | 1 | 8 |
| 57 | 1 | 1 | 7 |
| 59 | 1 | 3 | 8 |
| 60 | 2 | 7 | 9 |
| 61 | 1 | 4 | 8 |
| 86 | 2 | 4 | 9 |
| 87 | 2 | 8 | 9 |
| 97 | 1 | 2 | 7 |
| 100 | 1 | 2 | 5 |
| 102 | 1 | 3 | 4 |
| 110 | 1 | 2 | 5 |
| 127 | 5 | 7 | 9 |
| 128 | 2 | 5 | 8 |
| 136 | 1 | 2 | 8 |
| 147 | 1 | 2 | 3 |
| 41 | 1 | 1 | 5 |
| 95 | 1 | 1 | 8 |
| 29 | 1 | 1 | 1 |
| 15 | 1 | 1 | 1 |
| 43 | 1 | 1 | 1 |
| 14 | 1 | 1 | 1 |
| 42 | 1 | 1 | 1 |
| 12 | 1 | 1 | 8 |
| 160 | 1 | 1 | 8 |
| 162 | 1 | 1 | 2 |
| 163 | 1 | 1 | 1 |
| 161 | 1 | 1 | 9 |
| 129 | 1 | 1 | 1 |
| 148 | 1 | 1 | 1 |
| 150 | 1 | 1 | 2 |
| 149 | 1 | 1 | 2 |
| 152 | 1 | 1 | 2 |
| 151 | 1 | 1 | 1 |
| 171 | 1 | 1 | 2 |
| 155 | 1 | 6 | 9 |
| 156 | 1 | 1 | 6 |

What is claimed is:

1. A compound of the formula

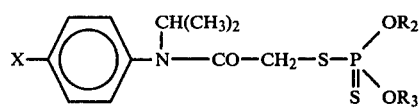

wherein
X is halogen and
$R_2$ and $R_3$ are selected from methyl and ethyl.

2. A compound of the formula

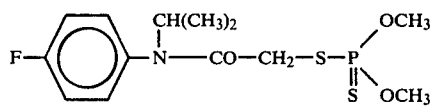

3. A compound of the formula

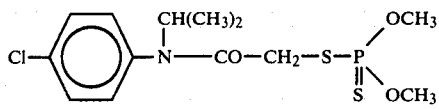

4. A compound of the formula

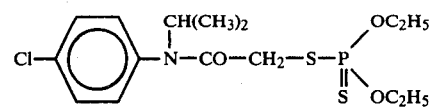

5. A compound of the formula

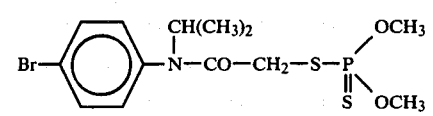

6. An herbicidal composition consisting essentially of an herbicidally effective amount of a compound as defined in claim 1.

7. A method of controlling weed grasses associated with crop plants without substantial damage to the crop plants which comprises applying to said weed grasses an herbicidally effective amount of an herbicidal agent of the general formula

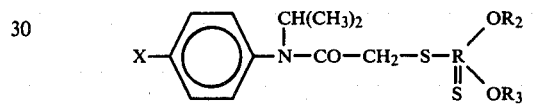

wherein X is halogen and $R_2$ and $R_3$ are selected from methyl and ethyl.

8. A method according to claim 7 wherein the herbicidal agent is

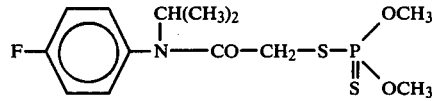

9. A method according to claim 7 wherein the herbicidal agent is

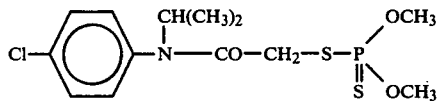

10. A method according to claim 7 wherein the herbicidal agent is

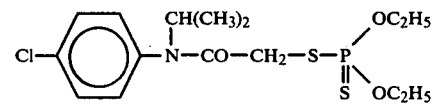

11. A method according to claim 7 wherein the herbicidal agent is

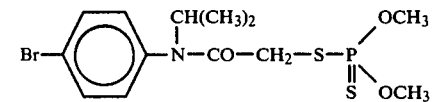

* * * * *